United States Patent [19]

Ebersole

[11] 4,219,335
[45] Aug. 26, 1980

[54] IMMUNOCHEMICAL TESTING USING TAGGED REAGENTS

[75] Inventor: Richard C. Ebersole, Newark, Del.

[73] Assignee: E. I. Du Pont de Nemours and Company, Wilmington, Del.

[21] Appl. No.: 942,261

[22] Filed: Sep. 18, 1978

Related U.S. Application Data

[63] Continuation-in-part of Ser. No. 848,217, Nov. 3, 1977, abandoned.

[51] Int. Cl.² .......................................... G01N 33/16
[52] U.S. Cl. .................................. 23/230 B; 23/915; 422/63; 422/69; 424/12; 324/71 R
[58] Field of Search .......................... 23/230 B; 424/12

[56] References Cited

U.S. PATENT DOCUMENTS

| | | | |
|---|---|---|---|
| 3,074,853 | 1/1963 | Brewer | 424/12 |
| 3,470,067 | 9/1969 | Warren | 210/222 |
| 3,826,619 | 7/1974 | Bratu | 23/230 B X |
| 3,853,467 | 12/1974 | Giaever | 23/230 B |
| 3,853,987 | 12/1974 | Dreyer | 424/1 |
| 3,904,367 | 9/1975 | Golibersuch | 23/230 B |
| 3,926,564 | 12/1975 | Giaever | 23/230 B X |
| 3,933,997 | 1/1976 | Hersh | 424/1 |
| 3,951,605 | 4/1976 | Natelson | 422/65 |
| 3,970,518 | 7/1976 | Giaever | 23/230 B X |
| 3,979,184 | 9/1976 | Giaever | 23/230 B X |
| 3,981,776 | 8/1974 | Saxholm | 23/230 B X |
| 3,985,608 | 10/1976 | Saxholm | 195/127 |
| 4,011,308 | 3/1977 | Giaever | 23/230 B X |
| 4,018,886 | 4/1977 | Giaever | 23/230 B X |
| 4,020,151 | 4/1977 | Bolz | 424/1.5 |
| 4,022,577 | 5/1977 | Brooker | 422/63 X |
| 4,041,146 | 8/1977 | Giaever | 424/1 |
| 4,054,646 | 10/1977 | Giaever | 424/12 |
| 4,067,959 | 1/1978 | Bolz | 23/230 B |
| 4,087,248 | 5/1978 | Miles | 422/63 X |

FOREIGN PATENT DOCUMENTS

2327547  5/1977  France .

OTHER PUBLICATIONS

M. Cais et al., Nature, 270 (5637), 534–535 (Dec. 8, 1977).
J. Guesdon et al., Immunochemistry, 14, 443–447 (1977).
Patent Abstracts DT 2,638,251 (German).
Patent Abstracts DT 2,651,388 (German).
Patent Abstracts GB 1,451,669 (U.K.).
Patent Abstracts CH 586,902 (Swiss).

*Primary Examiner*—Sidney Marantz

[57] ABSTRACT

The presence of a particular immunochemically reactive substance in a biological fluid can be determined using immune reagents tagged with particles which have characteristics capable of affecting electrical reactance.

10 Claims, 2 Drawing Figures

IMMUNOCHEMICAL TESTING USING TAGGED REAGENTS

CROSS REFERENCE TO RELATED APPLICATION

This application is a Continuation-in-Part of application Ser. No. 848,217, filed Nov. 3, 1977, now abandoned.

BACKGROUND OF THE INVENTION

This invention relates to a method for determining the presence of selected immunochemically responsive substances such as antibodies or antigens in body fluids. These selected substances will be referred to hereinafter as analytes.

The determination of such analytes provides much useful medical information. For example, pregnancy testing, syphilis testing and blood factor testing are all now done by conventional immunochemical methods. Most of these methods involve a visual inspection for the formation of precipitated or agglutinated antigen-antibody complexes. These methods sometimes require several replications at different reagent ratios to insure accuracy and also require an individual visual inspection for each test result. Use has also been made of radioactive and fluorescent tags to avoid the subjective visual determination. However, these methods sometimes have problems either in the use of expensive or transient tags, or in sensitivity or in safety and handling of radioactive materials. The method of this invention uses immune reagents tagged with particles such as magnetic materials which are safe to handle and which can be detected readily with highly sensitive and readily available electronic equipment. This method is readily adaptable to automated or semi-automated operation.

The use of magnetic particles in serological testing is known, but prior to this invention the magnetic particles have been used only to remove or sequester various components from a liquid sample. For example, U.S. Pat. Nos. 4,018,886 and 3,970,518, teach the use of magnetically active particles to collect selected proteins, followed by cleaving the proteins from the magnetic particles and a visual examination for precipitated proteins. Hersh et al., U.S. Pat. No. 3,933,997, teaches the use of magnetic particles to concentrate radioactive tags on a test substance.

None of the references teach the use of magnetic detection to obtain the desired result.

SUMMARY OF THE INVENTION

The presence or absence in a body fluid of an analyte, such as a specific antigen or antibody, can be determined by depositing a sample of the body fluid on a surface coated with a receptor reagent specifically reactive with the analyte. It the analyte is present, it will form a complex with the receptor reagent. The surface is then contacted with an immune reagent comprising an immune component which is specifically reactive with either the receptor reagent or with a complex of the receptor reagent and the analyte. The immune reagent also comprises particles which have characteristics capable of affecting electrical reactance. That is, they are minute fragments which alter the permittivity, conductivity or magnetic permeability of the surface. These particles will be referred to in this case as reactance tags. Metal or metal oxide particles are preferred, and magnetically active particles are more preferred. The immune reagent is generally applied to the surface as a liquid suspension. Unreacted immune reagent is then removed from the surface and the surface is examined for changes in dielectric constant, conductivity or magnetic permeability. In a direct test, the immune reagent is reactive with the receptor reagent-analyte complex and if the reactance tags are found to be attached to the surface, the presence of the analyte in the body fluid is indicated. Similarly, in an indirect test, the immune reagent is reactive with the receptor reagent but not with the receptor reagent analyte complex. If no reactance tags are detected on the surface, the presence of the analyte in the body fluid is indicated. In a competitive test the body fluid and immune reagent are deposited on the surface simultaneously. The amount of reactance tags on the surface is a measure of the amount of analyte in the body fluid. This system may be used manually, but it is readily adaptable to automated operation.

DETAILED DESCRIPTION OF THE INVENTION

Figure 1:
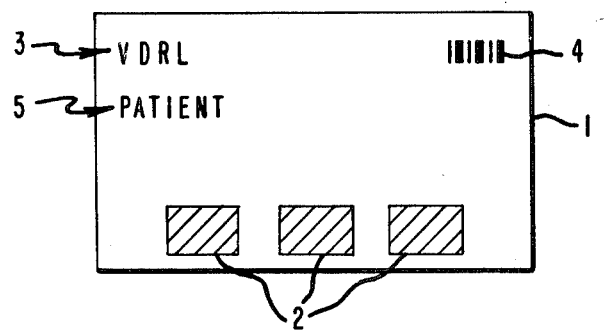
FIG. 1 is a drawing of a test card useful in this invention.

Conventional means can be used to detect the presence of the reactance tags on the test surface. For example, if the reactance tags affect the dielectric properties of the surface, a capacitance measurement will reveal whether the particles are present. In another example, if the particles are magnetic, magnetic pick-up heads such as those found in standard tape recording equipment may be used. Capacitive, conductive and magnetic permeability measurements that do not require direct contact with the test surface are preferred, but measurements using direct contact between the surface and the detector are not excluded. In order for the presence of the particles to be detected, it is preferable that the test surface be inert with respect to the property to be measured. However, it is possible to arrange the receptor reagent on the surface in bands or to induce a periodic magnetization on the surface as that produced by a magnetic tape recording system and then to move the surface at a particular rate past a detector which will monitor frequency. The detected frequency will be a function of the arrangement of the bands of receptor reagent or induced periodic magnetization and the rate of movement of the surface. Thus, the test surface itself need not be entirely free from electrical reactance to be considered inert for the purposes of this invention. In a preferred system for detecting the presence of magnetic tag, the test surface is adjacent to a reference surface coated with magnetic particles. Following the immune reactions, both the test surface and the reference surface can be magnetized in a periodic fashion. The detector circuit can be made to detect only the portion of the signal from the test surface which is in phase with the signal from the reference surface. This arrangement decreases the effects of system noise and provides increased sensitivity.

The test surface must also be capable of bonding with the receptor reagent and non-interfering with the test result. The surface can be flat or it can have depressions or dimples in which each test is conducted. While many materials are suitable test surfaces, plastic cards or tapes are preferred. The test surface on which receptor reagent is bonded may be within enclosed plastic packs or pouches. These packs can also contain the immune reagents in a separate area designed for addition to the test surface following sample addition.

The presence of a change in electrical reactance such as magnetic activity can be determined, even when a very small amount of the reactance tags is present. Therefore, each test will usually require only a droplet of body fluid and the test area can be very small. Consequently, a large number of discrete test areas and if desired, reference areas, can be arrayed on a single card or tape. The discrete areas may be either a series of tests for different select proteins or a series of tests for the same protein where the concentration of immune reagent on the test surface is varied over a range to give an indication of not only the presence of the select protein but also its approximate concentration in the body fluid.

The receptor reagent can be attached to the test surface by surface adsorption, gel entrapment, covalent bonding or other similar methods. Of these, covalent bonding is preferred. Any system of receptor attachment capable of orienting the reagent molecules on the test surface so that they will have maximum activity is also preferred. Receptor reagents include not only antibodies, but also tissue or cellular receptor proteins, serum transport proteins and lectins. Of these, antibodies probably have the widest applicability. Other classes of compounds, such as chelating agents, may also serve as useful receptor reagents if they react with the substance to be determined in the body fluid with sufficient specificity to avoid false results caused by competing reactions.

The materials useful as reactance tags which combine with immune compounds to form the immune reagents are those which will alter the electrical reactance of the test surface. That is, these materials, if distributed as a finely divided powder on the test surface, alter the dielectric, conductive or the magnetic properties of the surface. The advantage of this invention resides in using particles which are detectable in very small quantities by very sensitive but well developed and readily available electrical components. Further, the use of such materials avoids the problems of transient activity and handling hazards which one encounters in the use of radioactive tags. The preferred materials are metals and metal oxides. The more preferred metals and metal oxides are those which exhibit ferromagnetism. Such materials can be reacted with the antibodies and applied to the test surface while in a demagnetized state. Once they have been applied, the entire surface can be exposed to a magnetic field to magnetize the particles for detection purposes. This magnetic activity is then readily detectable by various well-known means such as a standard magnetic tape system or Hall effect detector. Magnetic materials include, but are not limited to, metals and alloys such as iron powder, nickel, cobalt, $CrO_2$, "Ferrofluid" (a ferromagnetic liquid produced by Ferrofluids Corp.), CoO, NiO, $Mn_2O_3$, magnetoplumbites, magnetic iron oxides and "Alnico", an alloy of aluminum, nickel cobalt and copper. Other useful materials are organic charge complexes with the high electrical conductivity such as N-methylphenazinum tetracyanoquinodimethane, $[Ce(NO_3)_6Mg(H_2O)_6]_3 \cdot 6H_2O$ crystal, $Bi_2Se_3$ crystals and tetrahiofulvalene complexes with tetrocyano-p-quinodimethane or $K_2Pt(CN_4)BrO_3 \cdot H_2O$ and amorphous materials with magnetic properties such as the chalcogenides, e.g., the europium chalcogenides and chalcogenide glass particles.

Preferred magnetic materials are the magnetic oxides of iron, cobalt, nickel, chromium and maganese and oxide coated particles of iron or nickel.

In order to provide sufficient surface area for bonding the immune compounds, it is preferred that the reactance tags have a large surface area, at least 100 $m^2/gm$. Particles in the range of 0.01 to 50 $\mu m$ in diameter are preferred.

These materials can be bonded to immune compounds by known techniques. The reactance tags can be encapsulated with an organic polymer to which the immune compounds can be bonded, or the surface can be silanized by conventional techniques. Organic compounds can then be attached to the silane linkage. U.S. Pat. No. 3,954,666 teaches polymer encapsulation of core materials and U.S. Pat. No. 3,983,299 teaches the use of silane linkages to bond organic compounds to inorganic particles. Techniques for immobilization of enzymes on magnetic supports which would be equally applicable to antibodies are described in methods in *Enzymology*, XLIV pp. 324-326. The manner of attachment of the reactive organic compounds to the reactance tags does not form the basis of this invention. Thus, other bonding methods may also be used so long as they do not interfere with the complexing ability of the immune compounds. The immune compounds are chosen to be specifically reactive with either the receptor reagents or with the complex of the receptor reagent with the body fluid substance to be determined.

Since the method of this invention utilizes electronic rather than visual inspection it is readily adaptable to automated operation. As used herein, the term "automated" is not meant to exclude the possibility that some of the operations may be performed manually. Referring to FIG. 1, a preferred test card 1 is shown having several areas 2 on which receptor reagents are bonded. Separate areas having different receptor reagents can be provided or the same receptor reagent can be bonded to each area in different concentrations. The card has a printed test identification 3, as well as a machine readable code 4, which contains the necessary information for automated operation. Optionally, the card can have a space 5, for entering a patient identification code.

Figure 2:
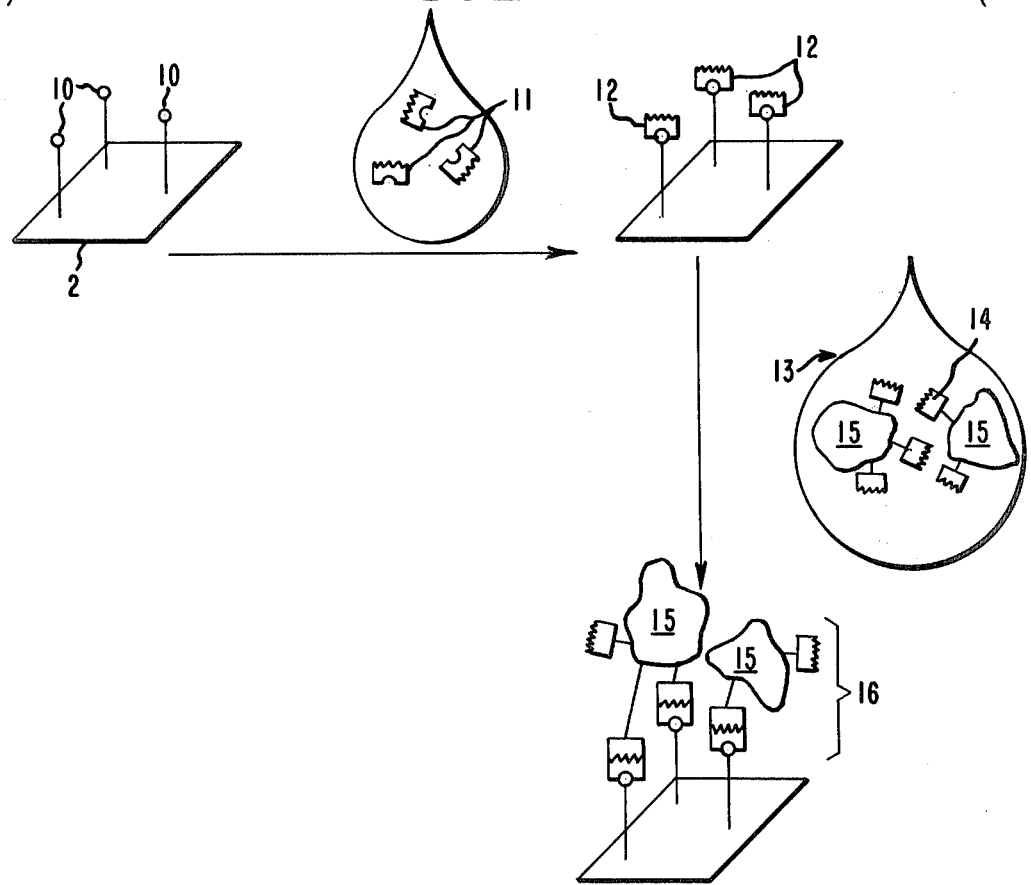
FIG. 2 is a schematic representation of the reactions involved in this invention.

FIG. 2 shows schematically a test area 2 of a test card of FIG. 1. Receptor reagents 10 are bonded to the test area. Patient body fluid containing the antibodies 11, the presence of which is to be determined is added to each test area. The antibody 11, if present, forms a complex 12 with the receptor reagent. The test area is then exposed to immune reagent 13 comprised of an immune compound 14 bonded to a reactance tag 15. This immune reagent forms complex 16 with the receptor reagent-patient antibody complex, if present, on the test area.

A preferred system for the practice of this invention would include a station for entering the necessary test cards for the desired test. Cards may be entered individually or in group as required. The cards are moved automatically to a sample addition station where a droplet of a patient's body fluid is applied to each of the test areas on the card. An automated device may include temperature control and a station for equilibration of the body fluid on the test areas for predetermined times. The card is then moved to a station where the immune reagent is applied to each of the test areas. Again, there may be temperature control and equilibration systems incorporated. Next, excess immune reagent is removed, and the card is then examined for the presence of reactance tags remaining in the test by measuring changes in electrical reactance of the card test areas.

It should be noted that in the particular embodiment described the test card is moved through each station. Other embodiments where each operation is conducted on a card maintained at a single location in an automated or semi-automated device are equally operable.

The method of this invention can be applied to the detection of a wide variety of materials including but not limited to antigens and antibodies of viral, bacterial, cellular and human origin in addition to hormones, drug metabolites and specific proteins. For example, the method is applicable to the detection of human autoantibodies, e.g, an antithyroglobulin; antigenic proteins such as complement factors, protein hormones, immunoglobulins and free light and heavy chains, e.g., thyroxine-binding globulin; and various species of microorganism antigens and antibodies such as hepatitis A and B virus. Application of this approach is primarily dependent on the availability of a suitable material to serve as a receptor reagent specifically reactive with the item to be determined.

EXAMPLE 1

In the determination of a human antibody, IgG, a serum sample can be prediluted with a protein buffer solution containing 0.12% bovine serum albumin and phosphate buffered saline at pH $7.7 \pm 0.2$. Sodium azide, 0.1%, an antimicrobial agent can be added in the diluent as a preservative.

The diluted patient sample can be quantitatively transferred to a test reaction card. The solid phase support consisting of anti-human IgG covalently bonded to derivatized polyamide sheets is prepared as follows:

Nylon-6 film (10 g) can be suspended in 3 N HCl (300 ml) and stirred at 30° C. for four hours, removed from the solution and washed exhaustively with water, ethanol and ether. The carboxyl content of a Nylon-6 film hydrolyzed for four hours is about 30–90 $\mu$Moles/gm.

The coupling of the antibody to the depolymerized Nylon-6 support can be carried out by carbodiimide activation. The overall reaction involves the condensation between the carboxyl group on the support and the amine groups of the antibody. The reaction is carried out in two steps.

One gram of the acid-treated Nylon-6 film is added to a solution of 50 mg of 1-cyclohexyl-3-(2-morpholinoethyl)-carbodiimide metho-p-toluenesulfate in 10 ml of water. The reaction mixture is adjusted to pH 4–5 with 6 N HCl, and the reaction allowed to continue at 30° C. for two-four hours. The film is then removed and washed several times with water to remove the excess carbodiimide.

The activated film is then introduced into a solution containing commercially available anti-human IgG in concentrations of 1 to 50 mg protein in 10 ml of water. After adjusting the solution to pH between 4–5, the reaction is continued for two to four hours at room temperature or overnight at 4° C. The reaction solution is then decanted and the film washed with water or buffer.

The test surface can then be equilibrated with the diluted sample for sufficient time to permit antibody binding to occur. The first equilibration may typically be about 30 minutes at 32° C. The reaction zones can then be washed with the same protein buffer solution and shaken to wash unabsorbed antigen from the surface.

The test reagent zones can then be immersed in an excess of goat anti-human IgG tagged with magnetic particles. For equilibration on the card, the immune particles are appropriately diluted in phosphate saline buffer at pH $7.5 \pm 0.5$ containing 0.12% bovine serum albumin. After equilibration, the test reaction surfaces can be washed with the BSA phosphate buffer at pH $7.7 \pm 0.2$.

The reaction surfaces are magnetized in a magnetic field and the test card processed through a detector capable of determining the presence of magnetic particles.

EXAMPLE 2

This Example demonstrates the determination of antibodies directed against specific antigens.

A serum sample was prediluted with a protein buffer solution containing 0.1% bovine serum albumin and Tris-(hydroxymethyl)-aminomethane (Tris) buffered at pH $6.5 \pm 0.4$. Sodium azide, 0.1%, an antimicrobial agent, was added in the diluent as a preservative.

The diluted sample was quantitatively transferred to a test reaction surface. The solid phase support, consisting of human serum albumin covalently bonded to either polyamide or polymethacrylic acid polymers, was prepared as follows:

The overall coupling reaction between albumin and films can involved cross linking between the amino or carboxyl groups of the film and protein. Cross linking can be achieved through the use of a polyfunctional aziridine reagent which is highly reactive with materials containing active hydrogens.

The films for attachment of the human serum albumin were first suspended in a 1% solution of XAMA polyfunctional aziridine (Cordova Chemical, Sacramento, California). Following stirring at 27° C. for thirty minutes, the films were removed from solution and washed with distilled water. The washed films were then stirred in a solution containing human serum albumin (1 mg/ml) for twelve hours at 4° C. The immobilized albumin film reagent can then be washed repetitively with Tris buffer (pH $6.5 \pm 0.4$) at 4° C. The washings are continued until no further albumin is released from the film. Representative levels of albumin attachment to the films are set out below:

| Film | ($\mu$g/cm$^2$) |
|---|---|
| Surface Groups | |
| Surlyn ® | 3.3 |
| Mylar ® ionomer resin | |
| polyester (Flame Treated) | 7.3 |
| No Surface Groups | |
| Polycarbonate | |
| Nylon (HCl Treated) | 16.0 |
| Activated Surface Groups | |
| Ethylene Maleic Anhydride | $\leq 1.0$ |

The test surface for anti-HSA was equilibrated with the diluted sample for sufficient time to permit anti-HSA binding. The reaction surface was then washed with the same Tris buffer solution (pH $7.4 \pm 0.4$) used in Example 1 to remove unattached sample debris from the surface.

The test reagent card was then immersed with excess of goat anti-human serum albumin tagged with magnetic particles. For equilibration, the immune anti-HSA particles were appropriately diluted in a Tris buffer a pH 6.5±0.5 containing 0.12% goat serum albumin. After equilibration the test reaction surfaces were washed free of unattached particles with the goat serum albumin Tris buffer.

The magnetic particles remaining on the reaction surface can be magnetized in response to a magnetic signal of known frequency. The test card can then be processed through a detector, capable of detecting the presence of the magnetic particles. The detection of the reactance properties of the test surface can be aided by the instrument techniques of phase lock application, phase sensitive rectification and other standard electronic amplification systems known to those skilled in the art.

As used herein, the phrase "consisting essentially of" is not used to exclude the additional operation steps or elements which do not prevent the advantage of this invention from being realized.

I claim:

1. A method for determining the presence of an analyte in a body fluid consisting essentially of
  a. contacting a surface with said fluid, said surface being coated with receptor reagents specifically reactive with said analyte;
  b. contacting the coated surface with immune reagent comprising immune compound specifically reactive with the receptor reagents or with a complex of the analyte and receptor reagent, said immune compound being coated on reactance tags which are particles capable of affecting electrical reactance;
  c. removing unreacted immune reagent from the surface; and
  d. measuring the electric reactance of the surface.

2. The method of claim 1 wherein the reactance tags are magnetically responsive.

3. The method of claim 1 wherein the reactance tags exhibit strong capacitive reactance.

4. The method of claim 1 wherein the reactance tags exhibit conductance.

5. The process of claim 1 wherein the reactance tags consist essentially of particles selected from the group consisting of metals and metal oxides.

6. The method of claim 5 wherein the particles are selected from the group consisting of the magnetic oxides of iron, cobalt, chromium, nickel and manganese and oxide coated particles of iron and nickel.

7. The method of claim 1 wherein said receptor reagent is bonded to said surface by adsorption, gel entrapment or covalent bonding.

8. The method of claim 1 wherein said receptor reagent is covalently bonded to said surface.

9. The method of claim 1 wherein said surface is attached to machine readable test information.

10. An automated analytical system including a test surface having a receptor reagent bonded thereto, said receptor reagent being specifically reactive with a component of a body fluid, a station for the application of a body fluid sample to said test surface, means for the application of an immune reagent to the test area, said immune reagent comprising immune compounds specifically reactive with the receptor reagent or with a complex of the receptor reagent with the component of the body fluid, said immune compounds being coated on reactance tags comprising particles which are capable of affecting electrical reactance, means for the removal of excess immune reagent, and means for the detection of reactance tags on said test area.

* * * * *